United States Patent
Horan et al.

(10) Patent No.: US 7,766,952 B2
(45) Date of Patent: Aug. 3, 2010

(54) DEPLOYMENT SYSTEM FOR A MEDICAL DEVICE

(75) Inventors: Steven Horan, Athlone (IE); Eamon Brady, Elphin (IE); Martin Keegan, Knocknacarra (IE)

(73) Assignee: Salviac Limited, Dublin (IE)

( * ) Notice: Subject to any disclaimer, the term of this patent is extended or adjusted under 35 U.S.C. 154(b) by 1011 days.

(21) Appl. No.: 11/448,146

(22) Filed: Jun. 6, 2006

(65) Prior Publication Data

US 2006/0286145 A1   Dec. 21, 2006

Related U.S. Application Data

(60) Provisional application No. 60/688,246, filed on Jun. 7, 2005.

(51) Int. Cl.
*A61F 2/06* (2006.01)
(52) U.S. Cl. .................................................. 623/1.11
(58) Field of Classification Search ............... 623/1.11, 623/1, 12, 902, 903; 254/134.3 R, 134 FT; 606/108
See application file for complete search history.

(56) References Cited

U.S. PATENT DOCUMENTS

| 5,263,963 | A | 11/1993 | Garrison et al. |
| 6,863,685 | B2 | 3/2005 | Davila et al. |
| 6,866,669 | B2 * | 3/2005 | Buzzard et al. ............. 606/108 |
| 2005/0222665 | A1 * | 10/2005 | Aranyi ....................... 623/1.11 |

* cited by examiner

*Primary Examiner*—Todd E Manahan
*Assistant Examiner*—Eric Blatt
(74) *Attorney, Agent, or Firm*—Sughrue Mion, PLLC; Jonathan Feuchtwang

(57) ABSTRACT

A delivery and deployment system for a self-expanding stent comprises a proximal handle having a rotatable thumbscrew and a sliding component which is attached to a distal stent restraining sheath. A rigid open coil spring is provided for converting rotation of the thumbscrew into translation of the sliding component). The spring is attached to the thumbscrew. The sliding component is located between adjacent coils of the spring. Rotation of the thumbscrew twists the spring and slowly slides the sliding component and hence the distal sheath in the proximal direction to uncover the stent, removing the constraint on the stent which is accurately deployed at the site of interest. The handle has a guide elongate channel which constrains the sliding component so that it cannot move in a rotational direction.

21 Claims, 12 Drawing Sheets

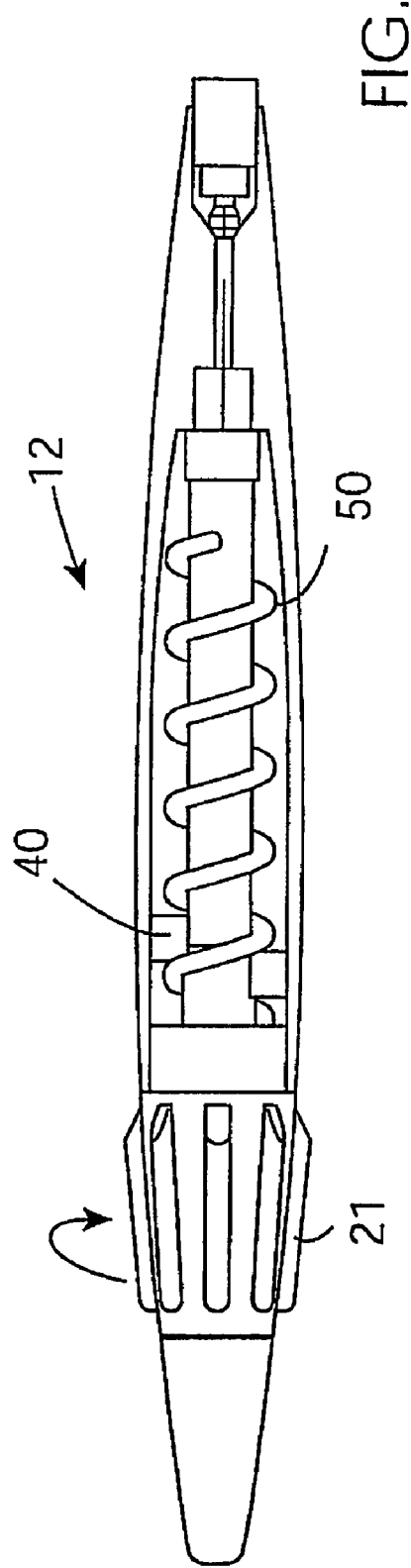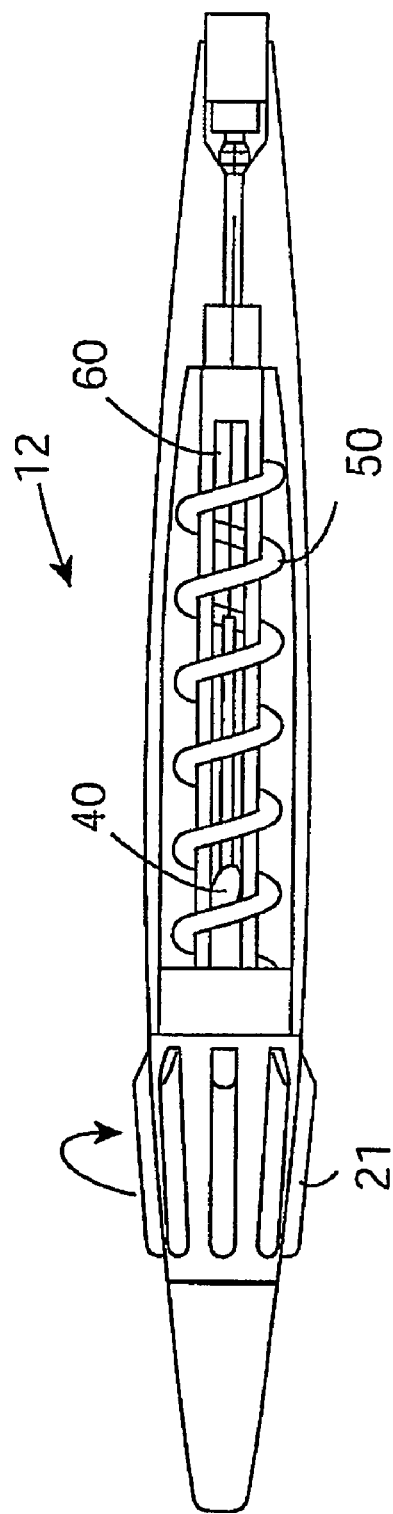

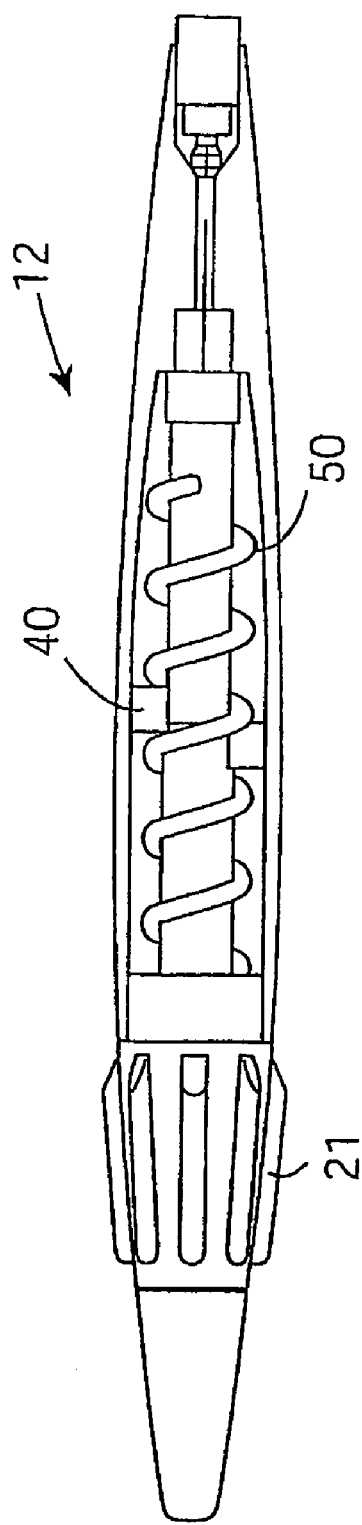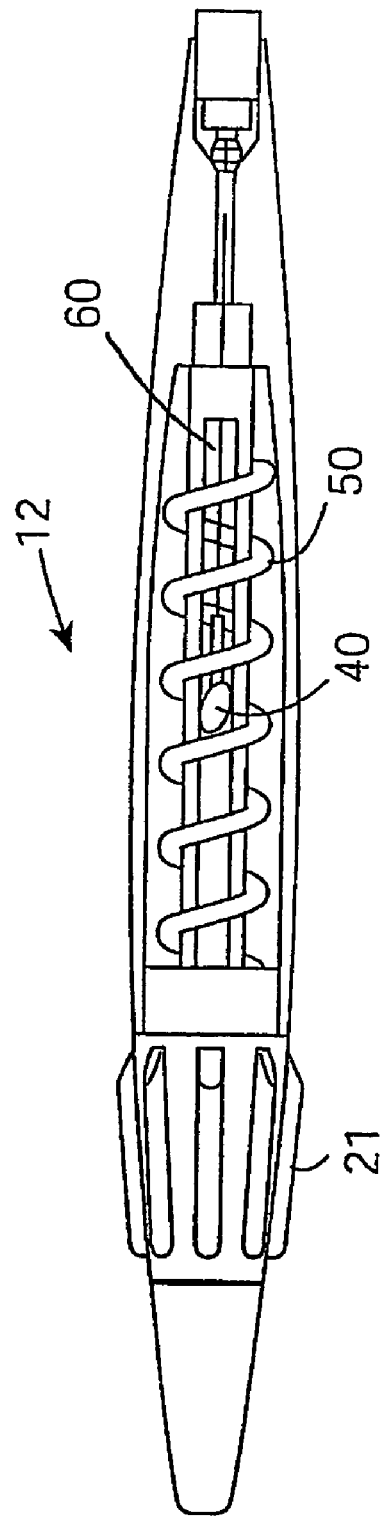
FIG. 4
FIG. 5

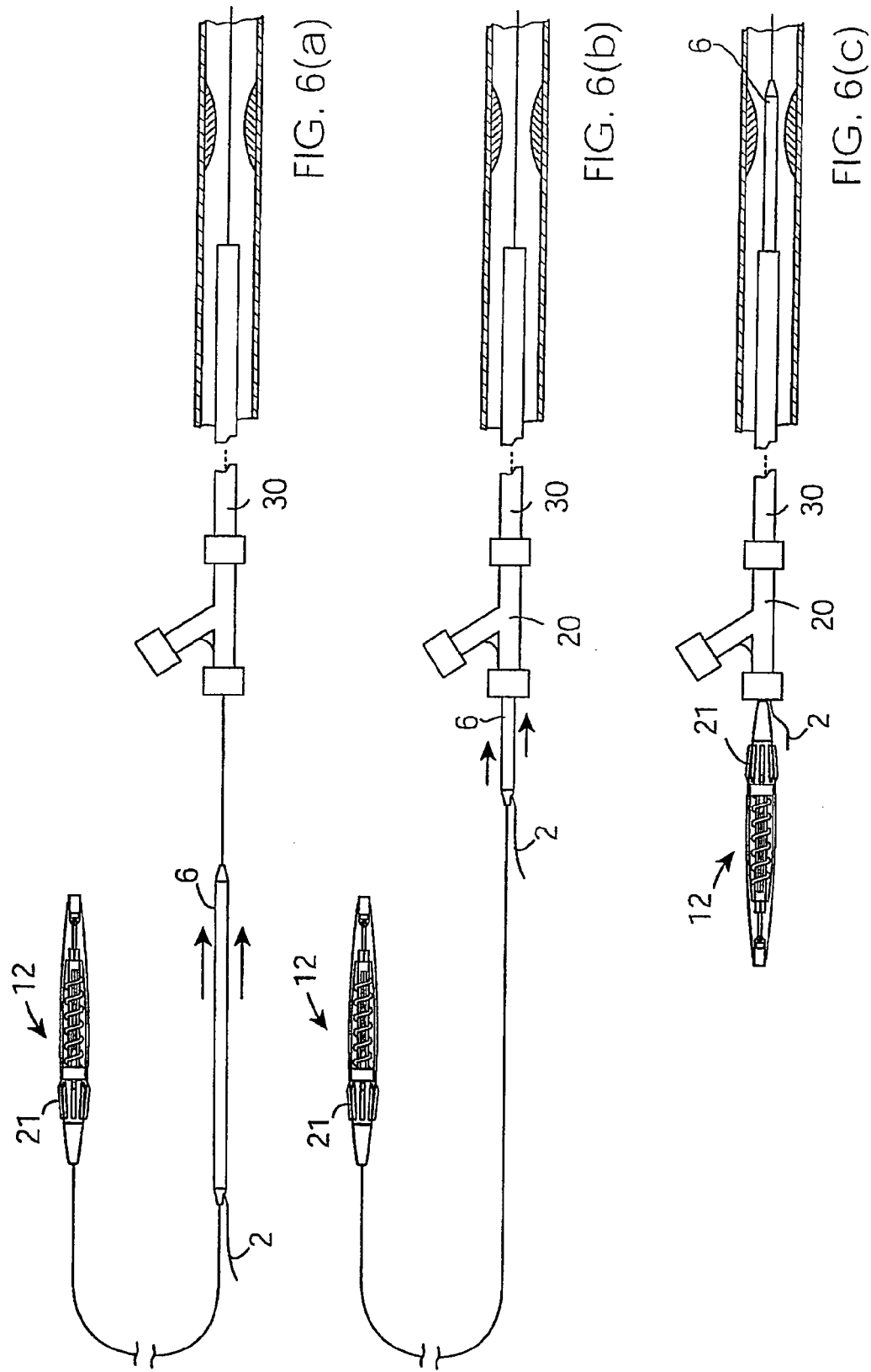

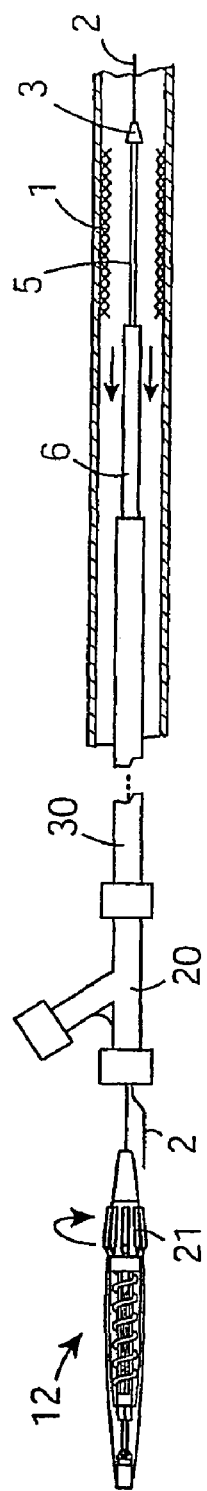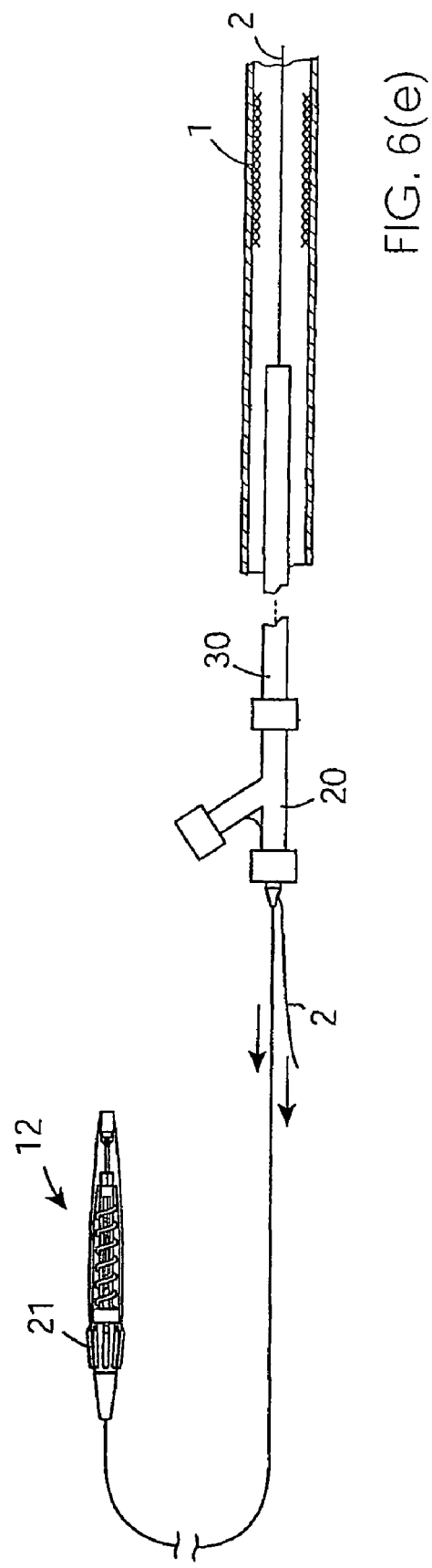
FIG. 6(d)
FIG. 6(e)

DEPLOYMENT SYSTEM FOR A MEDICAL DEVICE

RELATED APPLICATIONS

This application claims the benefit of priority to provisional application Ser. No. 60/688,246, filed Jun. 7, 2005.

FIELD OF INVENTION

This invention relates to a deployment system for deployment of a medical device, such as a stent, at a desired vascular location.

BACKGROUND OF INVENTION

Vascular intervention is today undertaken to treat a large number of diseases that had heretofore been treated by surgery. Stents are used widely in a number of applications to provide structural support to vessels that are being treated.

Stents are commonly used in the repair of aneurysms, as liners for vessels, or to provide mechanical support to prevent the collapse of stenosed or occluded vessels. Stents are typically delivered in a compressed state to a specific location inside the lumen of a vessel or other tubular structure, and then deployed at that location in the lumen to an expanded state. A stent has a diameter in its expanded state which is several times larger than the diameter of the stent in its compressed state. Stents are also frequently deployed in the treatment of atherosclerotic stenosis in blood vessels, especially after percutaneous transluminal coronary angioplasty (PTCA) procedures, to improve the results of the procedure and to reduce the likelihood of restenosis.

Stent designs are broadly divided into two categories, balloon expandable stents and self-expanding stents. The invention relates particularly to the delivery and positioning of self-expanding stents. The term self-expanding refers to the inherent material properties of the stent which cause the expansion of the stent once an external constraint has been removed. The effect is most commonly achieved by using a shape memory metallic alloy, such as nitinol.

Generally, stents are delivered to the desired location by means of a catheter, specifically referred to as a delivery catheter. Delivery catheters are threaded through a guiding catheter to the site of the disease and once the correct position has been established by means of fluoroscopic or other imaging method, the stent is deployed.

Delivery systems for self expanding stents generally comprise an inner component or core about which the stent is positioned in a retracted or reduced diameter and an outer sheath surrounding the stent. The stent is deployed by retracting the outer sheath relative to the inner component. This has the effect of removing the constraint on the stent which, on release, expands into an increased diameter deployed configuration. The procedure is controlled by a clinician by manipulating various components outside of the vasculature.

Conventional stent delivery systems suffer from the disadvantage that they are generally difficult to use to achieve accurate deployment of a stent at a desired site.

There is therefore a need for an improved deployment system which will address at least some of these problems.

SUMMARY OF INVENTION

According to the invention there is provided a deployment system for a medical device, comprising:
a movable sheath covering a medical device; and
an operator handle, the handle including a rotatable element associated with a sliding member, the sliding member coupled to the movable sheath and configured to transverse along a path in response to a rotational force applied to the rotatable element, the path defined by a coil spring.

In one embodiment of the invention the handle includes a translucent portion formed therein to provide an indicator of distance traveled by the sliding member.

The coil spring may be an open coil spring. The coil spring may be rigid. The coil spring may be coated with a material to reduce friction between the spring and the sliding member. The coil spring may have a variable pitch. The coil spring may have a consistent pitch. A proximal end of the coil spring may be coupled to the rotatable element of the handle.

The coil spring may have a cross-sectional profile selected from the group consisting of square, rectangular, oval and round. The coil spring may be disposed within the handle under compression to provide initial energy to overcome frictional forces associated with initial movement of the sliding member.

In another aspect of the invention there is provided a deployment system for a medical device, comprising:
a shaft assembly including a fixed inner member and a slidable outer member;
a handle assembly including a non-rotating portion and a rotating portion;
a guide member associated with the non-rotating portion of the handle assembly and extending therethrough, the fixed inner member associated with the guide member;
a coil spring disposed about the guide member; and
a sliding component having at least one projection configured to engage a path defined by the coil spring, the sliding component further associated with the slidable outer member, wherein rotation of the rotating portion of the handle assembly causes the sliding component to move along the path of the coil spring.

In one embodiment of the invention a proximal end of the coil spring is coupled to the rotating portion of the handle assembly.

In one case the sliding component includes a plurality of spring engaging grooves, the spring engaging grooves being formed having a pitch complementary to that of the coil spring. As the sliding component advances along a length of the coil spring, compression of the coil spring may impart a linear force to the sliding component. The distal end of the coil spring may be constrained linearly, thereby causing the pitch of the coil spring to increase as the sliding component advances along a length of the coil spring.

The non-rotating portion of the handle assembly may further include at least one slot formed therein, the slot configured to engage at least one projection of the sliding component to resist rotation of the sliding component.

The coil spring may have a cross-sectional profile selected from the group consisting of square, rectangular, oval and round. The coil spring may be disposed within the handle assembly under compression to provide initial energy to overcome frictional forces associated with initial movement of the sliding component.

The non-rotating portion of the handle assembly may include a translucent portion formed therein to provide an indicator of distance traveled by the sliding component.

According to another aspect of the invention there is provided a deployment system for a medical device such as a stent comprising a sheath for covering a medical device during delivery and an operator handle for deployment of the medical device, the handle having a rotatable component for rotation by a user, a sliding component connected to the sheath, and an actuator for converting rotation of the rotatable component into translation of the sliding component, the actuator comprising a coil spring, the sliding component being located between adjacent coils of the spring, rotation of the rotatable component moving the sliding component linearly to move the sheath and deploy the medical device.

In one embodiment the spring is an open coil spring, such as an open coil rigid spring.

The handle may have a guide for guiding the sliding component to move linearly. The guide may comprise a guide channel in the handle.

In one embodiment the sliding component is movable proximally to deploy the medical device.

The rotatable component may comprise a thumbscrew.

BRIEF DESCRIPTION OF THE DRAWINGS

The invention will be more clearly understood from the following description of some embodiments thereof, given by way of example only, with reference to the accompanying drawings, in which:

FIG. 2 is a side view of the handle of FIG. 1 in one position of use;

FIG. 3 is a plan view of the handle of FIG. 1 in the position of FIG. 2;

FIG. 4 is a side view of the handle of FIG. 1 in another position of use;

FIG. 5 is a plan view of the handle of FIG. 1 in the position of FIG. 4;

FIGS. 6(a) to 6(e) are side views illustrating the operation of the deployment system of FIG. 1.

DETAILED DESCRIPTION

Figure 1:
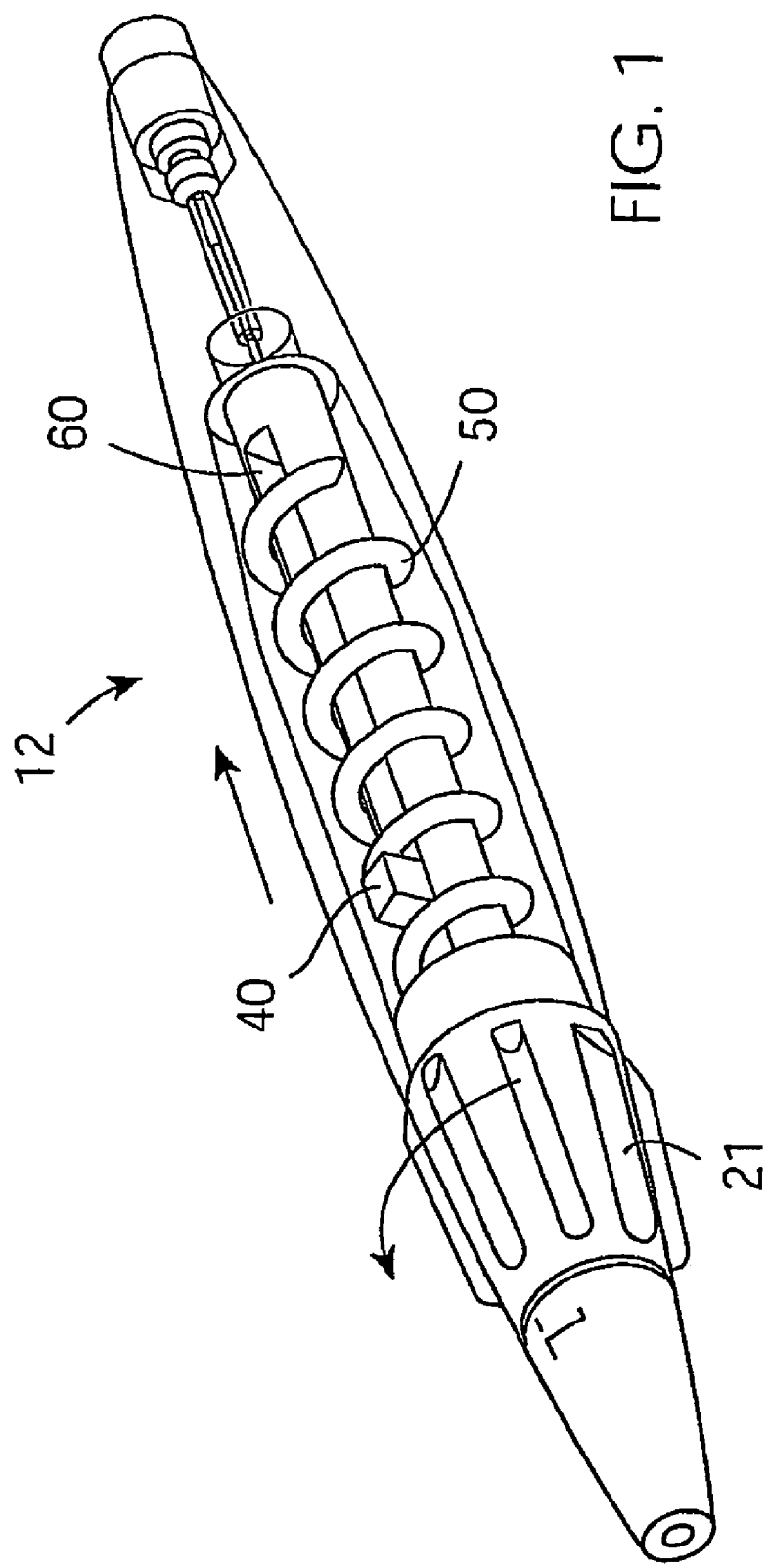
FIG. 1 is a perspective, partially cut-away view of a handle of a deployment system of the invention.

Referring to the drawings, and initially to FIGS. 6(a) to 6(e) thereof, there illustrated a delivery and deployment system according to the invention for a stent 1, which is of the self expanding type. The system is in this case configured for use with a guidewire 2 of the rapid exchange type.

The system comprises an inner core 5 with a distal tip 3 about which the stent 1 is located and a distal sheath 6 which retains the stent 1 in a compressed configuration during delivery through the vasculature of a patient to a deployment site, as illustrated for example in FIG. 6(c). To deploy the stent 1 the sheath 6 is drawn proximally relative to the inner core 5 and the stent 1 expands into a deployed configuration, as illustrated for example in FIG. 6(d) and 6(e).

The inner core 5 is fixed at the distal end to a larger diameter outer core 3, the difference in diameter providing a step for engagement with the stent 1 for deployment. The inner and outer core are fixed to a handle 12 at the proximal end. The outer distal sheath 6 is connected to a catheter shaft at the distal end and the catheter shaft is connected at the proximal end to a deployment/actuating mechanism which in this case is operated by a thumbscrew 21, rotation of the screw 21 being converted into linear movement of the sheath 6.

The catheter shaft and the guidewire 2 in this case extend through a standard Touhy Borst fitting 20 to which a guide catheter 30 is attached.

Referring in particular to FIGS. 1 to 5 the handle 12 has a rotatable component provided by the thumbscrew 21 and a sliding component 40 which is attached to the sheath 6. An actuator for converting rotation of the thumbscrew 21 into translation of the sliding component 40 comprises a rigid open coil spring 50 attached to the thumbscrew 21. The sliding component 40 is located between adjacent coils of the spring 50. Rotation of the thumbscrew 21 twists the spring 50 and slowly slides the sliding component 40 and hence the outer sheath 6 in the proximal direction to uncover the stent 1, removing the constraint on the stent 1 which is accurately deployed at the site of interest. The handle 12 has a guide which in this case is provided by an elongate channel 60 which constrains the sliding component 40 so that it cannot move in a rotational direction. During deployment, the spring 50 is under tension and to prevent undesirable extension of the spring 50, the spring 50 should be of a rigid material such as steel. The wall thickness of the wire forming the spring 50 may be relatively large and/or the spring 50 may be restrained at the proximal end to prevent extension of the spring 50.

The deployment system is relatively easy to manufacture as simple components are employed. The spring 50 is lightweight and occupies a small space.

To achieve minimal friction between moving parts, the spring 50 may be coated with a suitable coating such as PTFE. The thumbscrew 21 may be of a soft tactile material.

It will also be appreciated that at least part of the handle outer may be transparent to provide an indicator to the user of the distance travelled by the sliding component 40 and hence the degree to which the stent 1 is deployed.

Figure 7:
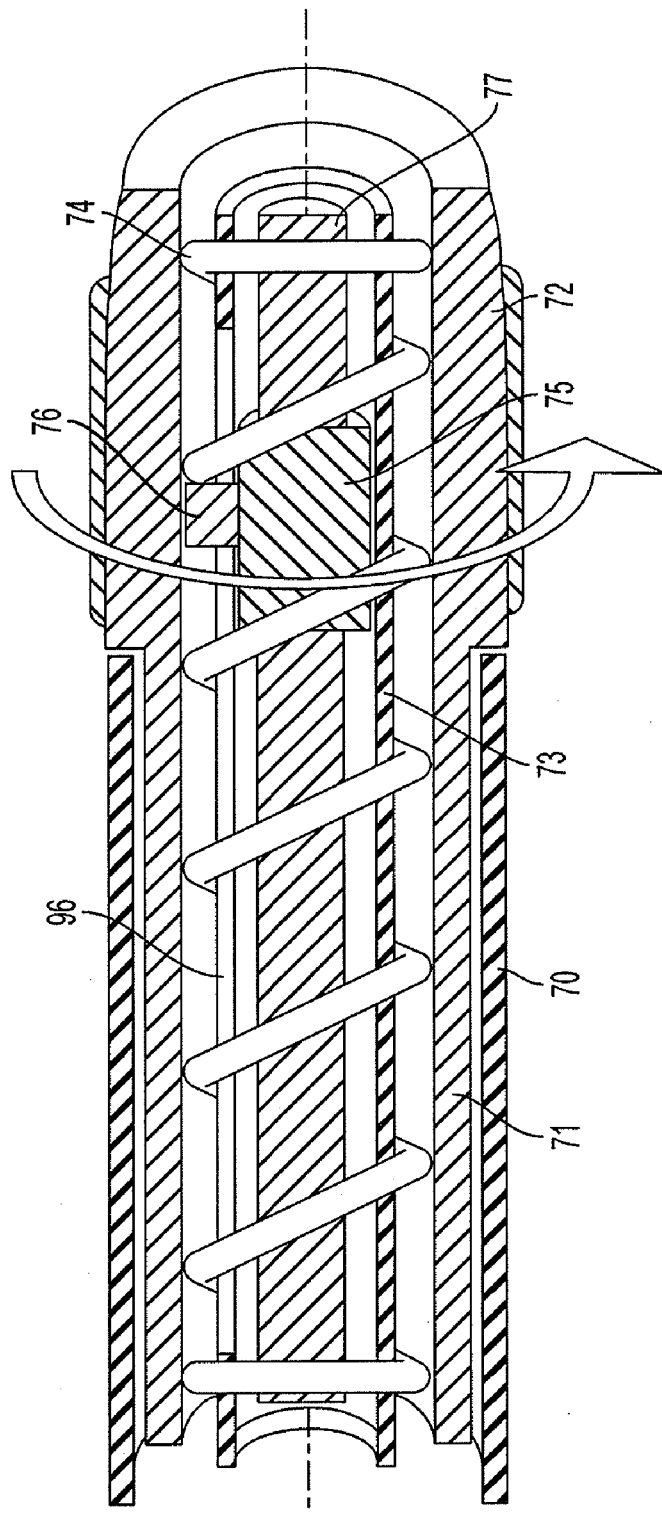
FIGS. 7 to 14 are cross sectional, side views illustrating deployment systems according to the invention with various springs.
Figure 8:
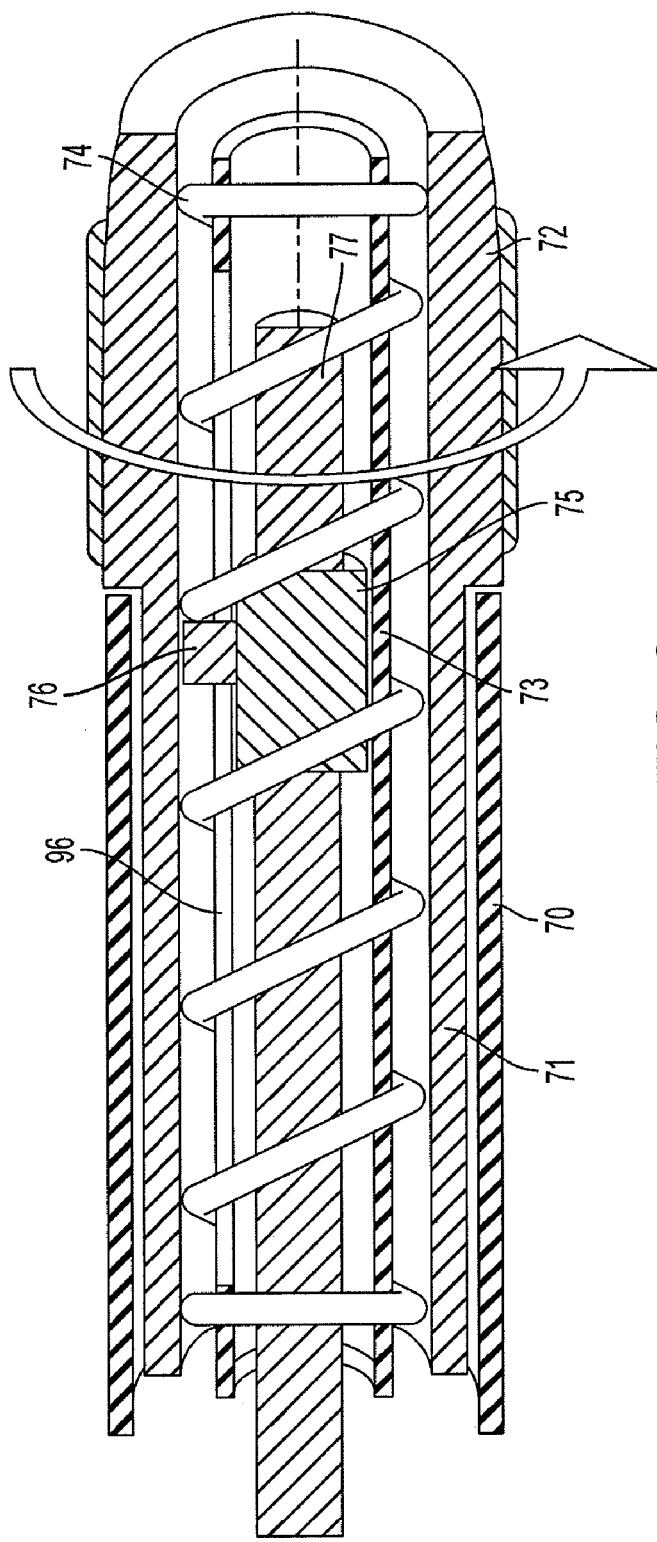

Referring to FIGS. 7 and 8 there is illustrated a deployment system comprising a non-rotating handle outer 70 and inner rotating component 71 having a thumbscrew 72. A non-rotating guide 73 extends axially through the handle and a spring coil 74 is disposed around the guide 73. The guide 73 has an elongate slot 96. A sliding component 75 has a projection 76 which extends through the slot 96 and abuts against the spring coil 74. A main catheter shaft 77 extends axially through the guide 73 and is fixed to the sliding component 75 at the handle end and to a sheath at a distal end of the stent deployment system. In FIG. 7 the sliding component 75 is towards a distal end of its travel. In FIG. 8 the sliding component 75 has been moved proximally for a distance corresponding to one spring pitch by a 360 degree rotation of the thumbscrew 72. The main catheter shaft 77 is correspondingly moved proximally and with it the stent covering sheath.

Figure 9:
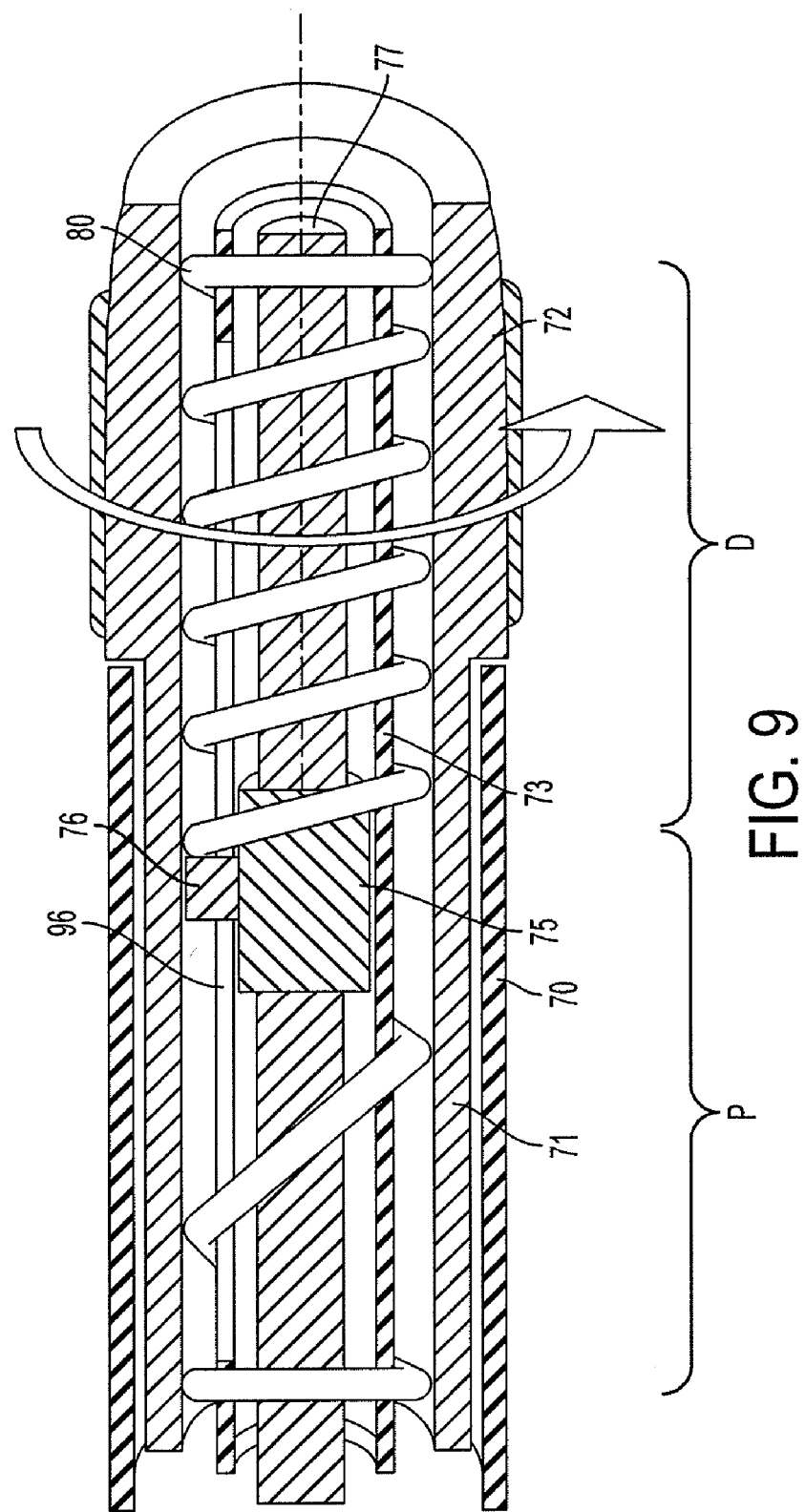

FIG. 9 illustrates a deployment system with a coiled spring 80 that compresses under the deployment force with a corresponding increase in mechanical advantage. In this case the proximal end of the spring 80 is constrained. Other details are as per FIGS. 7 and 8 above and like parts are assigned the same reference numerals. The same effect may be achieved by using a rigid spring that has a variable pitch. A low pitch at the distal end D provides high mechanical advantage and a low rate of sheath retraction. With a higher pitch at the proximal end P there is a lower mechanical advantage and a higher rate of sheath retraction. In this way the retraction of the sheath can be finely tuned to the stent being deployed, especially a self expanding stent.

Figure 10:
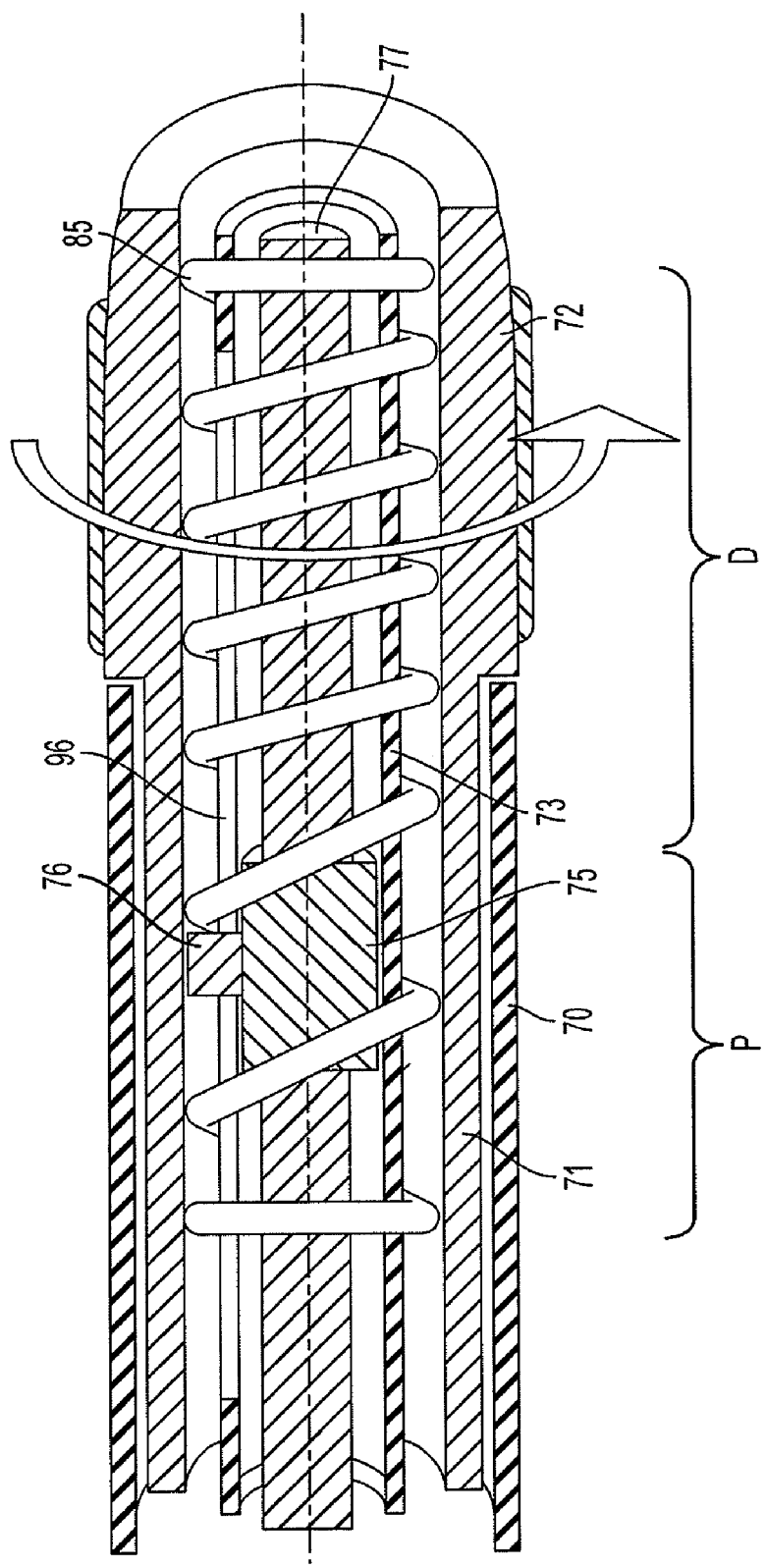

Referring to FIG. 10 there is illustrated another deployment system similar to FIGS. 7 and 8 and like parts are again assigned the same reference numerals. In this case the spring 85 has a reduced pitch at the distal end D to give an increased mechanical advantage, the spring 85 being in compression at the distal end. The proximal end P of the spring 85 is free to translate and there is no change in pitch at the proximal end.

Figure 11:
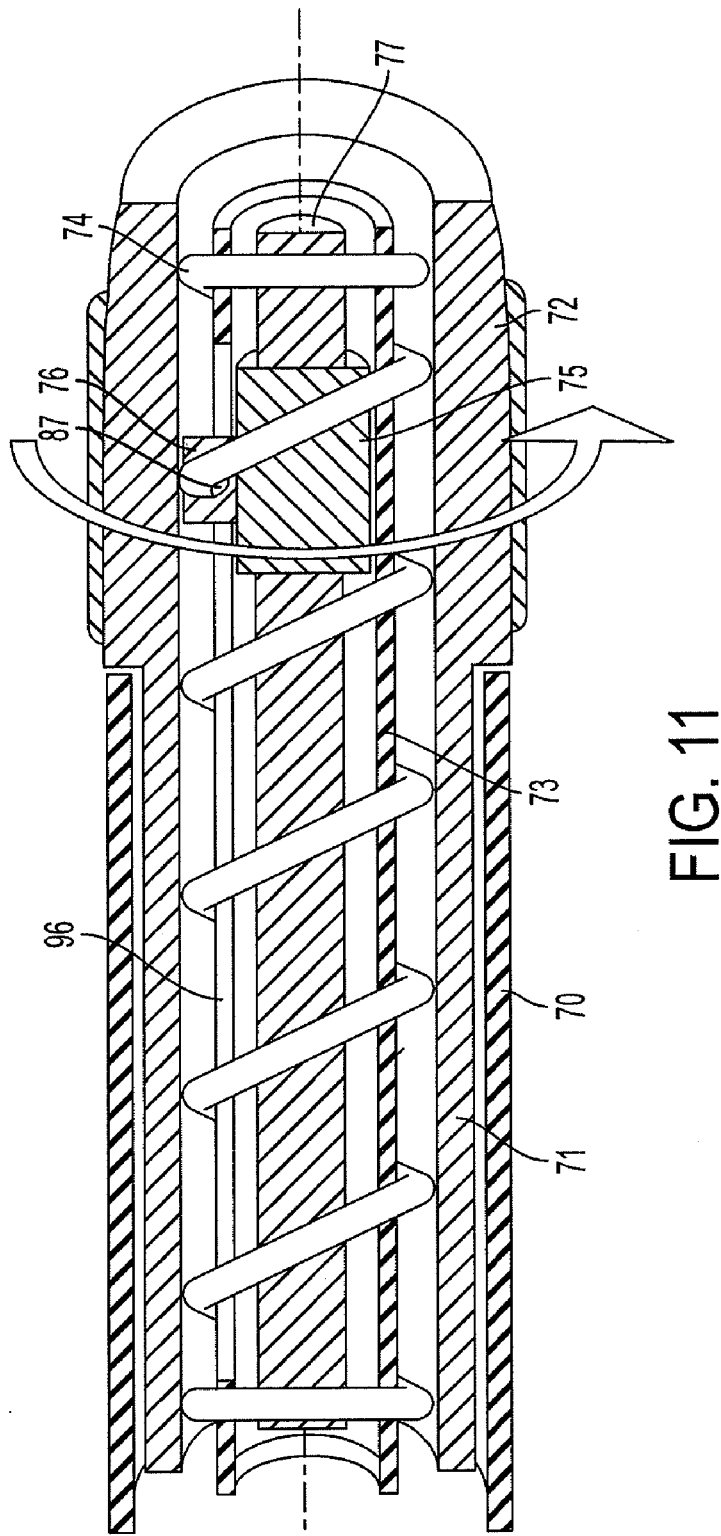

The arrangement of FIG. 11 is similar to that of FIGS. 7 and 8 except that in this case the projection 76 of the sliding component 75 has a spring engaging channel or groove 87. The spring 74 is in direct contact with the sliding component 75 with increased control.

Figure 12:
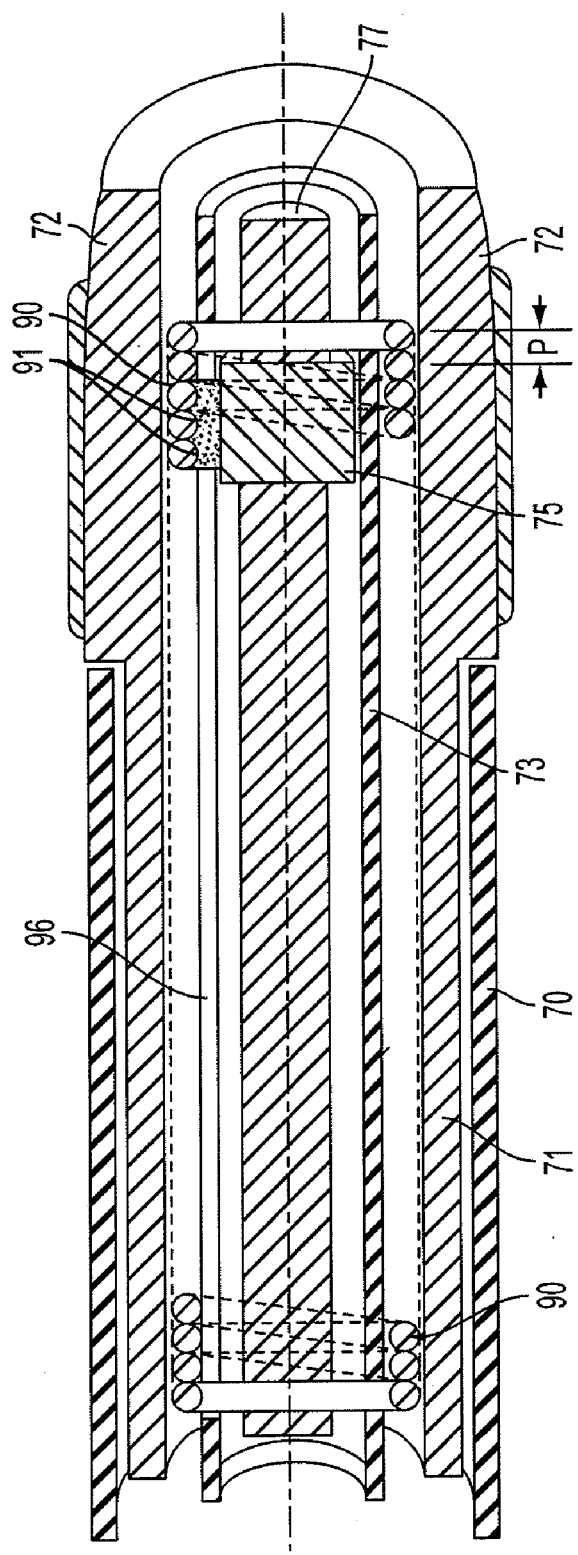

Referring to FIG. 12, in this case the deployment system comprises a closed spring coil 90 and the projection 76 of the sliding component 75 has a number of spring engaging grooves 91 such that the sliding component engages directly with the spring coil 90. The pitch P of the spring is very small leading to a high mechanical advantage.

Figure 13:
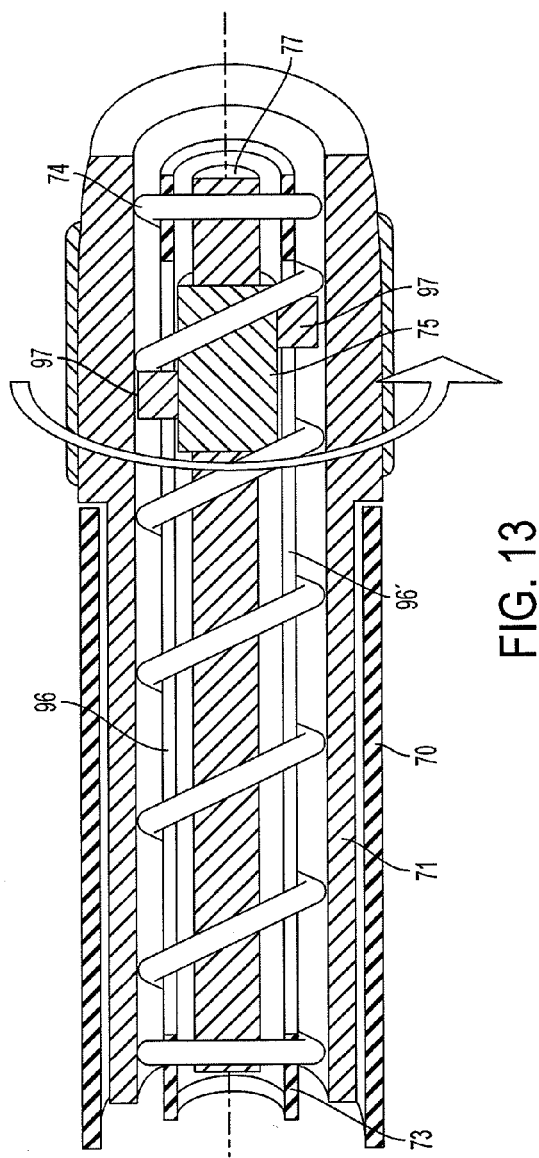

Referring to FIG. 13 there is illustrated another deployment system in which the non-rotating guide 95 has two slots 96 top and bottom which are engagable by corresponding projections 97 of the sliding component 75. Thus, the sliding component is in abutment with the spring 74 at two locations for even greater control.

Figure 14:
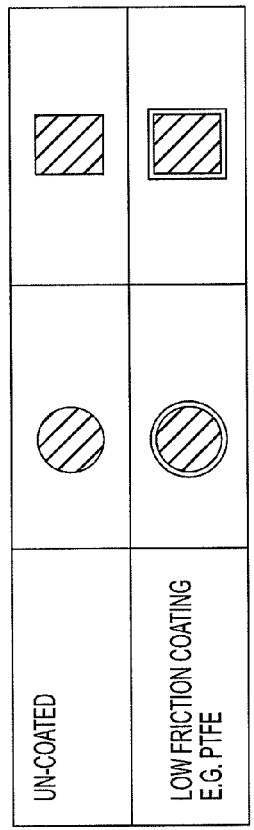

It will be appreciated that the various springs may be of any suitable cross sections, some of which are illustrated in FIG. 14. The springs may be coated with any suitable coating such as a low friction coating, for example PTFE.

Various other arrangements are possible. For example, the spring may be in compression to provide initial energy for overcoming the initial high resistance and pushing the distal end of the stent out of the delivery sheath.

The invention is not limited to the embodiments hereinbefore described, with reference to the accompanying drawings, which may be varied in construction and detail.

The invention claimed is:

1. A deployment system for a medical device, comprising:
   a movable sheath covering a medical device; and
   an operator handle, the handle including a rotatable element associated with a sliding member, the sliding member coupled to the movable sheath and configured to traverse along a path in response to a rotational force applied to the rotatable element, the path defined by a coil spring.

2. The deployment system of claim 1, wherein the handle includes a translucent portion formed therein to provide an indicator of distance traveled by the sliding member.

3. The deployment system of claim 1, wherein the coil spring is an open coil spring.

4. The deployment system of claim 1, wherein the coil spring is rigid.

5. The deployment system of claim 1, wherein the coil spring is coated with a material to reduce friction between the spring and the sliding member.

6. The deployment system of claim 1, wherein the coil spring has a variable pitch.

7. The deployment system of claim 1, wherein the coil spring has a consistent pitch.

8. The deployment system of claim 1, wherein a proximal end of the coil spring is coupled to the rotatable element of the handle.

9. The deployment system of claim 1, wherein the coil spring has a cross-sectional profile selected from the group consisting of, square, rectangular, oval and round.

10. The deployment system of claim 1, wherein the coil spring is disposed within the handle under compression to provide initial energy to overcome frictional forces associated with initial movement of the sliding member.

11. The deployment system of claim 1, wherein the path defined by the coil spring is made up of spacing within the coil spring.

12. A deployment system for a medical device, comprising:
   a shaft assembly including a fixed inner member and a slidable outer member;
   a handle assembly including a non-rotating portion and a rotating portion;
   a guide member associated with the non-rotating portion of the handle assembly and extending therethrough, the fixed inner member associated with the guide member;
   a coil spring disposed about the guide member; and
   a sliding component having at least one projection that is configured to engage a path defined by the coil spring, the sliding component further associated with the slidable outer member, wherein rotation of the rotating portion of the handle assembly causes the sliding component to move along the path of the coil spring.

13. The deployment system of claim 12, wherein a proximal end of the coil spring is coupled to the rotating portion of the handle assembly.

14. The deployment system of claim 12, wherein the sliding component includes a plurality of spring engaging grooves, the spring engaging grooves being formed having a pitch complementary to that of the coil spring.

15. The deployment system of claim 12, wherein as the sliding component advances along a length of the coil spring, compression of the coil spring imparts as linear force to the sliding component.

16. The deployment system of claim 15, wherein the distal end of the coil spring is constrained linearly, thereby causing the pitch of the coil spring to increase as the sliding component advances along a length of the coil spring.

17. The deployment system of claim 12, wherein the non-rotating portion of the handle assembly further includes at least one slot formed therein, the slot configured to engage the at least one projection of the sliding component to resist rotation of the sliding component.

18. The deployment system of claim 12, wherein the coil spring has a cross-sectional profile selected from the group consisting of, square, rectangular, oval and round.

19. The deployment system of claim 12, wherein the coil spring is disposed within the handle assembly under compression to provide initial energy to overcome frictional forces associated with initial movement of the sliding component.

20. The deployment system of claim 12, wherein the non-rotating portion of the handle assembly includes a translucent portion formed therein to provide an indicator of distance traveled by the sliding component.

21. The deployment system of claim 12, wherein the path defined by the coil spring is made up of spacing within the coil spring.

* * * * *